(12) United States Patent
Quintero

(10) Patent No.: US 8,734,379 B2
(45) Date of Patent: May 27, 2014

(54) FETAL SHUNT

(76) Inventor: Ruben A. Quintero, Coral Gables, FL (US)

( * ) Notice: Subject to any disclaimer, the term of this patent is extended or adjusted under 35 U.S.C. 154(b) by 0 days.

(21) Appl. No.: 13/510,433

(22) PCT Filed: Nov. 18, 2010

(86) PCT No.: PCT/US2010/057187
§ 371 (c)(1),
(2), (4) Date: May 17, 2012

(87) PCT Pub. No.: WO2011/063094
PCT Pub. Date: May 26, 2011

(65) Prior Publication Data
US 2013/0006162 A1    Jan. 3, 2013

Related U.S. Application Data

(60) Provisional application No. 61/262,210, filed on Nov. 18, 2009.

(51) Int. Cl.
*A61M 5/00* (2006.01)

(52) U.S. Cl.
USPC ............................................................ 604/8

(58) Field of Classification Search
USPC ............................................................ 604/8
See application file for complete search history.

(56) References Cited

U.S. PATENT DOCUMENTS

| 3,540,451 | A | * | 11/1970 | Zeman | 604/27 |
| 4,240,434 | A | * | 12/1980 | Newkirk | 604/9 |
| 4,382,445 | A | * | 5/1983 | Sommers | 604/8 |
| 4,474,569 | A | | 10/1984 | Newkirk | |
| 4,475,898 | A | | 10/1984 | Brodner et al. | |
| 4,631,051 | A | * | 12/1986 | Harris | 604/9 |
| 4,773,431 | A | * | 9/1988 | Lodomirski | 600/582 |
| 5,176,664 | A | * | 1/1993 | Weisman | 604/317 |
| 5,431,171 | A | * | 7/1995 | Harrison et al. | 600/511 |

(Continued)

FOREIGN PATENT DOCUMENTS

| DE | 202006018049 | | 8/2007 | |
| WO | 2008010001 | | 1/2008 | |
| WO | 2008-112865 | A1 | 9/2008 | |
| WO | WO 2008112738 | A1 * | 9/2008 | A61B 17/11 |

OTHER PUBLICATIONS

ISR for corresponding Application No. PCT/US2010/057187, KR as the ISA. mailed Aug. 18, 2011, 4 pages.

(Continued)

*Primary Examiner* — Susan Su
*Assistant Examiner* — Guy K Townsend
(74) *Attorney, Agent, or Firm* — Mark Terry

(57) ABSTRACT

A medical device, system, and method are described for treating in utero a fetus with a lower urinary tract obstruction. An implantable medical device may have a flexible catheter and an anchor. The catheter may define a proximal port, a distal port, a longitudinal axis, and a lumen providing fluid communication between the ports. The anchor may be affixed to the catheter at a position between the ports, and may have a resilient proximal member and a resilient distal member spaced a longitudinal distance apart, the proximal member and distal member each extending radially outward with respect to the longitudinal axis. An elongate delivery member may be releasably affixed to the medical device, and the medical device may be delivered through a tubular sheath defining a sheath lumen.

1 Claim, 3 Drawing Sheets

(56) References Cited

U.S. PATENT DOCUMENTS

| | | | |
|---|---|---|---|
| 5,538,005 A * | 7/1996 | Harrison et al. | 600/511 |
| 5,566,680 A * | 10/1996 | Urion et al. | 600/561 |
| 5,921,952 A * | 7/1999 | Desmond et al. | 604/8 |
| 5,951,497 A * | 9/1999 | Wallace et al. | 600/587 |
| 5,984,879 A * | 11/1999 | Wallace et al. | 600/587 |
| 6,231,524 B1 * | 5/2001 | Wallace et al. | 600/587 |
| 6,248,100 B1 * | 6/2001 | de Toledo et al. | 604/540 |
| 6,264,624 B1 * | 7/2001 | Desmond et al. | 604/8 |
| 6,510,600 B2 * | 1/2003 | Yaron et al. | 29/428 |
| 6,547,761 B2 * | 4/2003 | Liu | 604/104 |
| 6,558,342 B1 * | 5/2003 | Yaron et al. | 604/9 |
| 6,562,024 B2 * | 5/2003 | Alvarez de Toledo et al. | 604/540 |
| 6,726,664 B2 * | 4/2004 | Yaron et al. | 604/265 |
| 6,893,418 B2 * | 5/2005 | Liu | 604/106 |
| 6,893,430 B2 * | 5/2005 | Eshel et al. | 604/544 |
| 7,481,816 B2 * | 1/2009 | Richter et al. | 606/108 |
| 7,524,302 B2 * | 4/2009 | Tower | 604/96.01 |
| 7,753,889 B2 * | 7/2010 | Rosenberg | 604/174 |
| 2001/0049494 A1 | 12/2001 | Liu | |
| 2001/0053890 A1 | 12/2001 | Osborne | |
| 2005/0148880 A1 * | 7/2005 | Tower | 600/470 |
| 2006/0079845 A1 | 4/2006 | Howard et al. | |
| 2007/0105168 A1 * | 5/2007 | Eghtesady | 435/7.32 |
| 2007/0225584 A1 * | 9/2007 | Gravenstein et al. | 600/376 |
| 2008/0044392 A1 * | 2/2008 | Kues et al. | 424/93.21 |
| 2008/0051704 A1 * | 2/2008 | Patel et al. | 604/95.05 |
| 2008/0112865 A1 * | 5/2008 | Alward et al. | 423/212 |

OTHER PUBLICATIONS

Supplementary EP Search Report, EP 10832161, dated Mar. 12, 2013.

* cited by examiner

FETAL SHUNT

FIELD OF THE INVENTION

The present invention relates to a method and system for medical treatment of a fetal lower urinary tract obstruction (and other conditions such as pleural effusion, ascites, cysts, and others) in utero.

BACKGROUND OF THE INVENTION

Fetal urethral abnormalities manifesting as lower urinary tract obstruction ("LUTO") are associated with significant morbidity and mortality. This sporadic condition occurs in approximately 1:5000-8000 male fetuses with the most common cause being posterior valves. In females, urethral atresia accounts for the majority of cases. Untreated, LUTO may lead to hydronephrosis, renal dysplasia, and perinatal death in up to 90% of patients. Prenatally diagnosed cases of posterior urethral valves have a 30-50% mortality. If oligohydramnios is present at the time of prenatal diagnosis, the mortality is as high as 77%. Death is attributed to pulmonary hypoplasia and renal dysplasia. To avert these complications, percutaneous vesicoamniotic shunts or open fetal vesicostomy have been previously performed in utero to treat these conditions.

Percutaneous ultrasound-guided vesicoamniotic shunting ("VAS") of fetuses with LUTO was first reported in the early 1980's. The goal of therapy is to avert pulmonary hypoplasia from the attendant oligohydramnios as well as to preserve renal function. Fetal vesicostomy via open fetal surgery was at one time proposed as a way to avoid the limitations of VAS, but did not gain acceptance and is thus only of historical interest. VAS is currently being offered only to patients without sonographic or biochemical evidence consistent with renal cystic dysplasia, normal karyotype, and lack of associated major congenital anomalies.

Despite adequate placement, malfunction of VAS may occur up to 60% of the time. The shunt may pull from the skin into the fetal abdomen, resulting in iatrogenic ascites, or out of the fetal bladder, with no further derivation of urine. The shunt may pull out of the fetus altogether as well. Replacement of the shunt is associated with an additive risk of fetal demise, chorioamnionitis, premature rupture of membranes and miscarriage or preterm delivery, for a total perinatal loss rate of approximately 4% per instance.

In 1995, endoscopy was introduced in the management of fetuses with LUTO. Endoscopy provided a new set of possibilities in these cases, including cystoscopy, ablation of posterior urethral valves, lysis of obstructive ureteroceles, fetal hydrolaparoscopy and fetal cystotomy, and endoscopic documentation of vesicoamniotic shunt placement. Results showed, however, that the differential diagnosis of type III posterior urethral valves and urethral atresia was very difficult or impossible to make, and that ablation of the valves could be technically challenging and inaccurate at times.

As a specific example of prior treatments, FIG. 9 is an ultrasound showing use of a conventional shunt, resulting in urinary ascites secondary to a dislodged shunt (indicated as 'S') in the fetal bladder (indicated as 'B') of a patient. Anhydramnios is also visible. Another specific example of a prior treatment is depicted in FIG. 10, which is a fetal hydrolaparoscopy image showing a prior art shunt which has embedded in the fetal bladder (indicated as 'B').

In view of the above, it is desirable to provide an effective medical device, system and method of fetal shunting for patients with fetal lower urinary tract obstruction.

SUMMARY OF THE INVENTION

The present invention advantageously provides a medical device, system and method for treating in utero a fetus with a lower urinary tract obstruction, an obstruction of another cavity, an ascite, a pleural effusion, a pericardial effusion, or a cyst, etc.

An implantable medical device may have a flexible catheter and an anchor. The catheter may define a proximal port, a distal port, a longitudinal axis, and a lumen providing fluid communication between the ports. The anchor may be affixed to the catheter at a position between the ports, and may have a resilient proximal member and a resilient distal member spaced a longitudinal distance apart, the proximal member and distal member each extending radially outward with respect to the longitudinal axis.

A medical shunt system may have an implantable medical device, an elongate delivery member, and a tubular sheath defining a sheath lumen. The implantable medical device may have an elongate flexible catheter and an anchor. The catheter may define a plurality of proximal ports, a plurality of distal ports, a longitudinal axis, and a catheter lumen providing fluid communication between the proximal ports and the distal ports. A proximal portion and a distal portion of the catheter each may have a curved pig-tail shape. The anchor may be affixed to the catheter at a position between the proximal ports and the distal ports. The anchor may have an inner trunk member, a resilient proximal member and a resilient distal member, the proximal member and distal member being spaced a longitudinal distance apart and each extending radially outward and circumferentially around the longitudinal axis. The elongate delivery member may be releasably affixed to the medical device. The medical device and delivery member may be in the sheath lumen in a delivery configuration, and the delivery member pushes the medical device distal of the tubular sheath in a deployment configuration.

A method of medical treatment of a fetus may include providing a sheath and a medical device, the medical device having a flexible catheter and an anchor affixed to the catheter. Then, a distal end of the sheath is moved into proximity with the fetus. A distal portion of the catheter and a distal member of the anchor may be advanced from a first position inside a lumen defined by the tubular sheath lumen to a second position inside the fetal bladder, allowing the distal member of the anchor to resiliently expand into a disk shape. A proximal portion of the catheter and the proximal member of the anchor may be maintained in a position outside the fetus. The sheath may be withdrawn in a proximal direction, allowing the proximal member of the anchor to resiliently expand into a disk shape. Fluids in the fetal bladder are allowed to enter the distal port, pass through the catheter lumen, and exit the proximal port.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 6 is an endoscopic image of the fetal bladder during fetal hydrolaparoscopy;

FIG. 7 is an ultrasound intraoperative image of the placement of a medical device;

FIG. 8 is an endoscopic image of the placement of the proximal end of a medical device;

FIG. 9 is an ultrasound image, showing urinary ascites secondary to a vesicoamniotic shunt according to the prior art dislodged in a fetal bladder; and FIG. 10 is a fetal hydrolaparoscopy image, showing the vesicoamniotic shunt according to the prior art of FIG. 9 embedded in the fetal bladder.

DETAILED DESCRIPTION OF THE INVENTION

Figure 1:
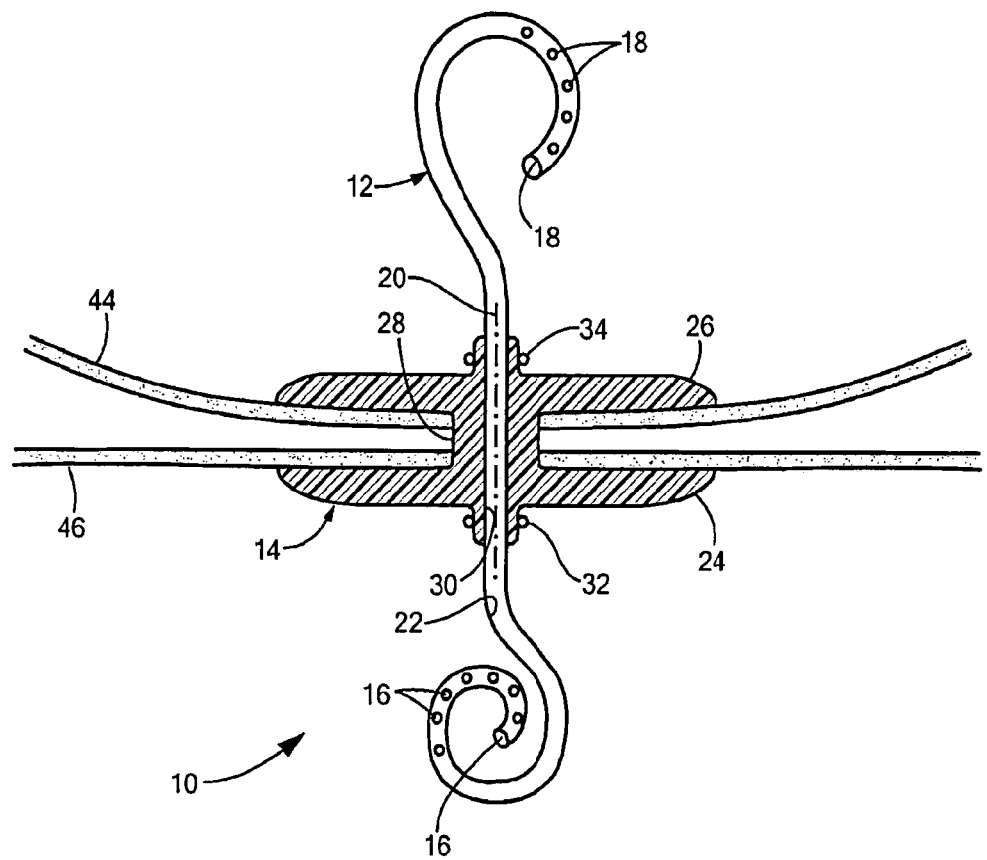
FIG. 1 is an illustration of an exemplary medical device constructed in accordance with the principles of the present invention.

The present invention advantageously provides a medical device, system and method of fetal shunting for patients with fetal lower urinary tract obstruction. Referring now to the drawings in which like reference designators refer to like elements, there is shown in FIG. 1 an exemplary embodiment of a device constructed in accordance with the principles of the present invention, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

The medical device 10 may be implanted to treat in utero a fetus diagnosed with a lower urinary tract obstruction, and may generally include creating or defining a fluid passage from inside the fetal bladder to an outer surface of the fetal skin. The fluid passage may be referred to as a shunt, and may take the form of a flexible tubular member such as for example a catheter tube or other tubular member.

Figure 3:
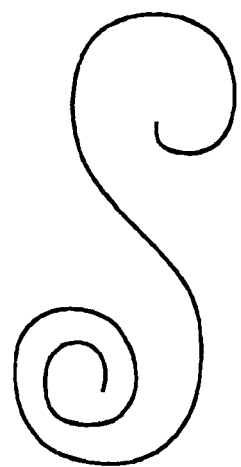
FIG. 3 is an illustration of a catheter component of the medical device of FIG. 1.

Specifically as shown in FIG. 1, the medical device 10 may include a flexible catheter 12 and an anchor 14. The catheter 12 may define one or more proximal ports 16, one or more distal ports 18, a longitudinal axis 20, and a lumen 22 providing fluid communication between the ports 16 and 18. A proximal portion and a distal portion of the catheter may each have a curved pig-tail shape, to enhance drainage and to fit within the enclosed spaces of the fetal bladder and the uterus. Accordingly, the tubular member may have the shape of a double pig-tail catheter as shown in FIG. 3.

Figure 4:
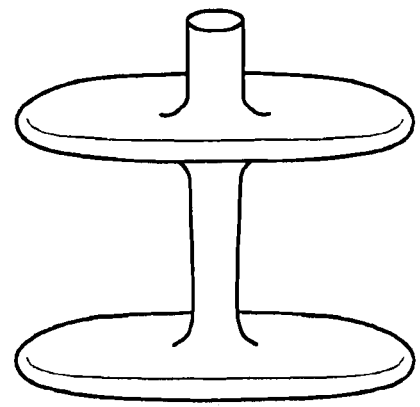
FIG. 4 is an illustration of an anchor component of the medical device of FIG. 1.
Figure 5:
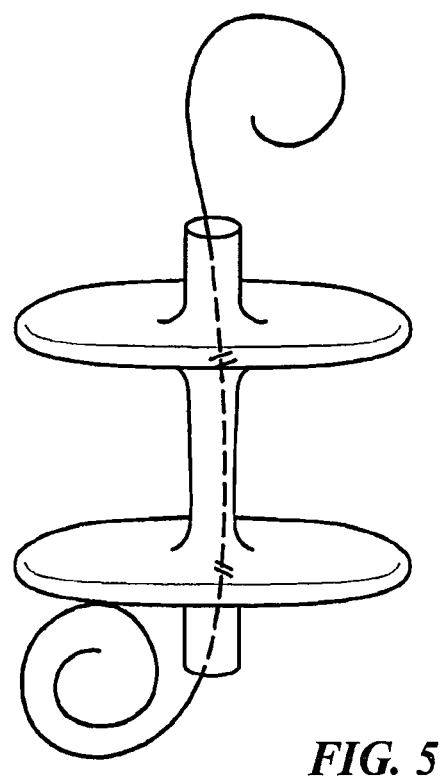
FIG. 5 is an illustration of an exemplary medical device constructed in accordance with the principles of the present invention.

The anchor 14 may be coupled to the tubular member to gently maintain the tubular member in the desired position, without being dislodged by growth or movement. The anchor 14 is affixed to the catheter 12 at a position between the ports 16 and 18, resisting undesired movement or dislodging of the catheter 12 once implanted. The anchor 14 may have a resilient proximal member 24 and a resilient distal member 26 spaced a longitudinal distance apart, and both of the proximal member 24 and distal member 26 may extend radially outward with respect to the longitudinal axis 20. The proximal member 24 and distal member 26 each extend radially outward and circumferentially around the longitudinal axis 20. The proximal member 24 and distal member 26 may both have a disk shape as shown in FIG. 4, or may have any other suitable shape such as for example a regular or irregular polygon, square, ellipse, etc. As a specific example, the anchor 14 may be of a shape useful for repair or treatment of an aperture defect such as for example an atrial septal occluder.

The proximal member 24 and the distal member 26 may be fastened directly to the catheter 12, or the anchor 14 may also have an inner trunk member 28 extending longitudinally between the proximal member 24 and the distal member 26. The trunk member 28 may define a longitudinal passage 30, and the catheter 12 may extend through the passage 30.

The medical device 10 may also include one or more fasteners to fasten the anchor 14 to the catheter 12. Any suitable type of fastener may be used, including for example a suture, stitch, staple, clip, clamp or other fastener. For example, a proximal fastener 32 and a distal fastener 34 may be provided, each fastening a portion of the catheter 12 and anchor 14 together.

Figure 2:
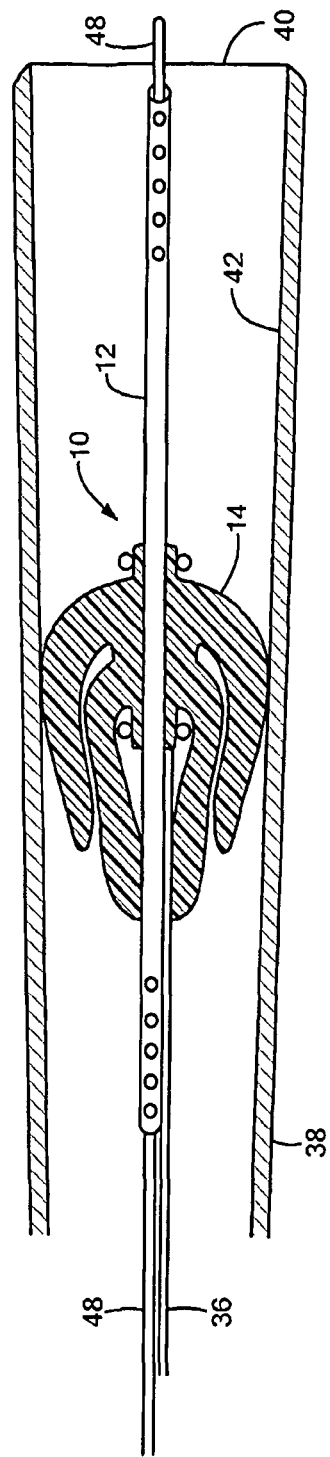
FIG. 2 is an illustration of the medical device of FIG. 1, in a delivery configuration.

A medical system is shown in a delivery configuration in FIG. 2. The medical system includes the implantable medical device 10 as shown in FIG. 1, and may also have an elongate delivery member 36, a tubular sheath 38, and a flexible guiding element such as for example a guidewire 48. The elongate delivery member 36 may be releasably affixed to the medical device 10. Delivery member may be any suitable elongate member, such as for example a guidewire. The delivery member 36 is illustrated in FIG. 2 as being coupled to a proximal portion of the anchor 14, but may alternatively be coupled to the catheter 12.

The tubular sheath 38 defines a delivery port 40 and a sheath lumen 42 in communication with the delivery port 40. The medical device 10 and delivery member 36 are in the sheath lumen 42 during delivery of the medical device 10 to a desired site for treatment, and the guidewire 48 passes through the lumen 22 of the catheter 12. The delivery member 36 may be used to deploy the medical device 10 by pushing it distal of the tubular sheath 38 into a deployment configuration.

A method of medical treatment of a fetus may include first providing a medical device 10 and a delivery sheath 38, the medical device 10 having a flexible catheter 12 and an anchor 14 affixed to the catheter 12. Then, a distal end of the sheath 38 is moved into proximity with the fetus. A distal portion of the catheter 12 and a distal member 26 of the anchor 14 may be advanced from a first position inside the lumen 42 defined by the tubular sheath 38 to a second position inside the fetal bladder 44. The distal member 26 of the anchor 14 may be allowed to resiliently expand into a disk shape. A proximal portion of the catheter 12 and the proximal member 24 of the anchor 14 should be maintained in a position outside the fetal skin 46. Then the sheath 38 is withdrawn in a proximal direction, allowing the proximal member 24 of the anchor to resiliently expand into a disk shape. Fluids in the fetal bladder 44 are allowed to enter the distal ports 18, pass through the catheter lumen 22, and exit the proximal ports 16.

If a delivery member 36 is provided, a distal portion of the catheter 12 and a distal member 26 of the anchor 14 may be advanced to the desired position by pushing on a proximal portion of the delivery member 36. The delivery member 36 may be releasably coupled to the medical device, so that the delivery member 36 may be uncoupled 36 from the medical device 10, after a distal portion of the catheter 12 and a distal member 26 of the anchor 14 have reached the desired position.

Also, if the medical device 10 is advanced too far, such that for example the proximal member 24 enters the fetal bladder 44, the medical device 10 may be withdrawn back into the sheath lumen 42 by pulling proximally on the delivery member 36. Accordingly, the anchor 14 or double-disk device allows bi-directional control by the physician.

The physician may confirm desired placement of the medical device 10, which may include evaluating the position of the proximal member, distal member, and a fastener fastening the catheter and anchor together, before withdrawing the sheath 38 from the patient in a proximal direction and uncoupling the delivery member 36 from the medical device. Confirming that the medical device is in the desired position and arrangement may be performed using any suitable technology, such as for example imaging equipment including ultrasound, an endoscope, or the like.

Endoscopy may be used, for example where a cystotomy may be performed to overcome the complication of fetal urinary ascites and partial bladder collapse from a prior diagnostic vesicocentesis. Endoscopy may also enable adequate revision of the medical device 10 in the fetal bladder. Finally, endoscopy allows confirmation of the correct placement of the proximal disk of the medical device 10 on the fetal skin.

Correct in utero deployment of the proximal member 24 and distal member 26 into the bladder and fetal skin, respectively, can be monitored by the operator with ultrasound. Should any of the anchor elements such as the proximal member 24 and distal member 26 not deploy in the correct cavity, the device can be reloaded into the delivery sheath and redeployed appropriately. This capability represents an advantage over prior shunting devices, including the double-basket catheter. Once the proximal member 24 and distal member 26 are confirmed to be in the target cavities, the wire guide may be unscrewed and the device becomes released. Adequate drainage of the target organ (bladder, peritoneal cavity, any other cystic cavity) is assured by attaching the double pig-tail catheter onto the anchor 14, with a proximal and a distal loop or other fastener 32 and 34 visible on ultrasound. Finally, endoscopic documentation of the correct placement of the proximal member 24 at the level of the fetal skin confirms the sonographic impression of the location of this end of the device.

In particular, the method may include an ultrasound examination of patients referred with a presumptive diagnosis of fetal LUTO, including fetal anatomy, biometry, amniotic fluid volume, placental location and transvaginal cervical length assessment. The fetal urinary tract may be assessed systematically for the presence or absence or renal hyperechogenicity, hydronephrosis or dysplasia, hydroureters, patent or competent ureterovesical junction, megacystis, bladder wall thickness and urethral diameter. Presence or absence of an upper pole moiety or gross evidence of an obstructive ureterocele may also be sought out.

Depending on the condition of the patient and any imaged or otherwise discerned symptoms identified through the ultrasound examination, a fetal hydrolaparoscopy may be performed. A small fetal cystotomy (approximately 4 mm) may be performed, enough to allow entry of an endoscope into the fetal bladder. The medical device 10 may be placed between the fetal bladder and skin, and positioning may be documented both sonographically and endoscopically. A follow-up ultrasound may later confirm the medical device 10 to be in the desired position, that the bladder is adequately drained, and a normal amount of amniotic fluid volume is present.

Images from an exemplary method of use for the above-described system are provided in FIGS. 7 and 8. In particular, FIG. 7 is an ultrasound intraoperative image of the placement of a medical device 10, where T is a trocar; B is a bladder; P is a proximal end of an anchoring device at the level of the skin; D is the distal end of the anchoring device inside the fetal bladder; and C is the distal end of a double pig-tail catheter.

FIG. 8 shows an endoscopic image of the placement of the proximal end of a medical device 10 at the level of the fetal skin. The proximal end of a double pigtail catheter is visible, as well as the metal wires and screw-in end of the anchoring device.

Accordingly, the present system provides a solution to fetal LUTO that can be reliably and effectively managed using medical device 10. This treatment constitutes an advance in fetal therapy, beyond the prior double pig-tail catheter without an anchoring device or ability to maintain its position either within the fetal bladder or at the fetal skin. Dislodgement of prior catheters may be caused by the retraction of the bladder wall from the fetal skin after shunting, or lack of firmness of the catheter or from extraction of the catheter by the fetus. In contrast, the medical device 10 resists becoming dislodged and being accidentally removed by movement of the fetus.

In conclusion, the present medical device, system and method provides for the in utero management and medical treatment of fetuses with lower urinary tract obstruction.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical shunt system, comprising:
   a tubular sheath designed for partial insertion into a fetal bladder, the sheath including a lumen; and
   a flexible implantable device for insertion into the sheath, the implantable device comprising:
      a flexible anchor comprising a proximal disk-shaped member, a distal disk-shaped member parallel to the proximal member, a trunk connecting the proximal and distal members, and a passage that extends through the trunk;
      an elongate flexible catheter extending through the trunk, the catheter defining a plurality of proximal ports, a plurality of distal ports, a longitudinal axis, and a catheter lumen providing fluid communication between the proximal ports and the distal ports, a proximal portion and a distal portion of the catheter each having a curved pig-tail shape when not under force from another member;
      a rigid guidewire for insertion into the catheter lumen and for maintaining the catheter in an elongate disposition when located within the lumen of the sheath;
      a rigid and elongate delivery member releasably fixed to the anchor, wherein the delivery member is designed to both push and pull the implantable device through the lumen of the sheath, and wherein the delivery member is designed to be released from the anchor after placement of the implantable device; and wherein the implantable device is designed to be compressed into the lumen of the sheath so as to be deployed into a fetal bladder.

* * * * *